US009146177B2

(12) United States Patent
Levijoki et al.

(10) Patent No.: US 9,146,177 B2
(45) Date of Patent: Sep. 29, 2015

(54) SYSTEM AND METHOD FOR DIAGNOSING A FAULT IN AN OXYGEN SENSOR BASED ON ENGINE SPEED

(71) Applicant: GM GLOBAL TECHNOLOGY OPERATIONS LLC, Detroit, MI (US)

(72) Inventors: Stephen Paul Levijoki, Swartz Creek, MI (US); Thomas J. Majcher, Orchard Lake, MI (US); Scott Jeffrey, Hartland, MI (US); John W. Siekkinen, Novi, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 174 days.

(21) Appl. No.: 13/672,231

(22) Filed: Nov. 8, 2012

(65) Prior Publication Data

US 2014/0033812 A1 Feb. 6, 2014

Related U.S. Application Data

(60) Provisional application No. 61/679,285, filed on Aug. 3, 2012.

(51) Int. Cl.
  *G01M 15/00* (2006.01)
  *G01M 15/10* (2006.01)
  *F01N 11/00* (2006.01)
  *F02D 41/14* (2006.01)
  (Continued)

(52) U.S. Cl.
  CPC .............. *G01M 15/10* (2013.01); *F01N 11/00* (2013.01); *F01N 11/007* (2013.01); *F02D 41/1454* (2013.01); *F02D 41/1495* (2013.01); *F02D 41/222* (2013.01); *G01N 27/4175* (2013.01); *G01N 33/007* (2013.01); *Y02T 10/40* (2013.01)

(58) Field of Classification Search
  CPC ............... F01N 11/007; G01M 15/104; F02D 41/1495; F02D 41/1454
  USPC ..................... 73/1.06, 23.32, 114.69–114.73; 123/435; 701/109, 114
  See application file for complete search history.

(56) References Cited

U.S. PATENT DOCUMENTS

| 4,214,308 A | 7/1980 | Carp |
| 4,928,518 A | 5/1990 | Tamura |

(Continued)

FOREIGN PATENT DOCUMENTS

| DE | 38 34 711 A1 | 4/1990 |
| DE | 4333412 A1 | 4/1995 |

(Continued)

OTHER PUBLICATIONS

U.S. Appl. No. 13/673,325, filed Nov. 9, 2012, Levijoki et al.

(Continued)

*Primary Examiner* — Eric S McCall
*Assistant Examiner* — Anthony W Megna Fuentes

(57) ABSTRACT

A system according to the principles of the present disclosure includes an error count module and a sensor diagnostic module. The error count module increases an error count when an actual air/fuel ratio is different from a desired air/fuel ratio and selectively adjusts the error count based on an actual engine speed. An oxygen sensor generates a signal indicating the actual air/fuel ratio. The sensor diagnostic module diagnoses a fault in the oxygen sensor when the error count is greater than a first predetermined count.

20 Claims, 5 Drawing Sheets

(51) Int. Cl.
*F02D 41/22* (2006.01)
*G01N 27/417* (2006.01)
*G01N 33/00* (2006.01)

(56) References Cited

U.S. PATENT DOCUMENTS

| | | | |
|---|---|---|---|
| 5,357,791 | A | 10/1994 | Gee et al. |
| 5,390,650 | A | 2/1995 | Gee et al. |
| 5,485,382 | A | 1/1996 | Seki et al. |
| 5,666,925 | A | 9/1997 | Denz et al. |
| 5,970,967 | A | 10/1999 | Uchikawa |
| 7,266,942 | B2 | 9/2007 | Iihoshi et al. |
| 7,549,284 | B2 | 6/2009 | Iihoshi et al. |
| 7,900,616 | B2 | 3/2011 | Saunders |
| 7,937,209 | B2 | 5/2011 | Dudek et al. |
| 2009/0182490 | A1 | 7/2009 | Saunders |
| 2013/0104626 | A1* | 5/2013 | Levijoki et al. ............ 73/23.32 |

FOREIGN PATENT DOCUMENTS

| | | |
|---|---|---|
| DE | 19518292 A1 | 11/1996 |
| DE | 694 05 615 T2 | 1/1998 |
| DE | 69407685 T2 | 4/1998 |
| DE | 103 31 334 A1 | 2/2005 |
| DE | 102008037634 A1 | 5/2009 |
| DE | 10 2010 022 683 A1 | 4/2011 |
| DE | 102012219626 A1 | 5/2013 |
| EP | 0616121 A1 | 9/1994 |
| EP | 1600619 A2 | 11/2005 |
| JP | H09242587 A | 9/1997 |

OTHER PUBLICATIONS

U.S. Appl. No. 14/074,790, filed Nov. 8, 2013, Levijoki et al.
U.S. Appl. No. 13/286,717, filed Nov. 1, 2011, Levijoki et al.
Office Action dated Sep. 10, 2014, from the German Patent Office for German Patent Application No. 10 2013 214 541.1; 7 pages.
Office Action dated Jan. 30, 2015, from the German Patent Office for German Patent Application No. 10 2013 222 502.4; 7 pages.

* cited by examiner

SYSTEM AND METHOD FOR DIAGNOSING A FAULT IN AN OXYGEN SENSOR BASED ON ENGINE SPEED

CROSS-REFERENCE TO RELATED APPLICATIONS

This application claims the benefit of U.S. Provisional Application No. 61/679,285, filed on Aug. 3, 2012. The disclosure of the above application is incorporated herein by reference in its entirety.

FIELD

The present disclosure relates to systems and methods for diagnosing a fault in an oxygen sensor based on engine speed.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

An oxygen sensor may be positioned in an exhaust system to measure oxygen levels in exhaust gas from an engine. The oxygen sensor may generate an oxygen signal indicating the oxygen levels. The oxygen signal may also indicate an air/fuel ratio of the engine, which may be referred to as an actual air/fuel ratio. The amount of air and fuel provided to cylinders of the engine may be controlled based on a desired air/fuel ratio, such as a stoichiometric air/fuel ratio, and the actual air/fuel ratio.

Fuel control systems may operate in a closed-loop state or an open-loop state. In the closed-loop state, fuel injection may be controlled to minimize differences between the desired air/fuel ratio and the actual air/fuel ratio. In the open-loop state, fuel injection may be controlled independent from the actual air/fuel ratio. For example, fuel injection may be controlled based on a fuel map.

SUMMARY

A system according to the principles of the present disclosure includes an error count module and a sensor diagnostic module. The error count module increases an error count when an actual air/fuel ratio is different from a desired air/fuel ratio and selectively adjusts the error count based on an actual engine speed. An oxygen sensor generates a signal indicating the actual air/fuel ratio. The sensor diagnostic module diagnoses a fault in the oxygen sensor when the error count is greater than a first predetermined count.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
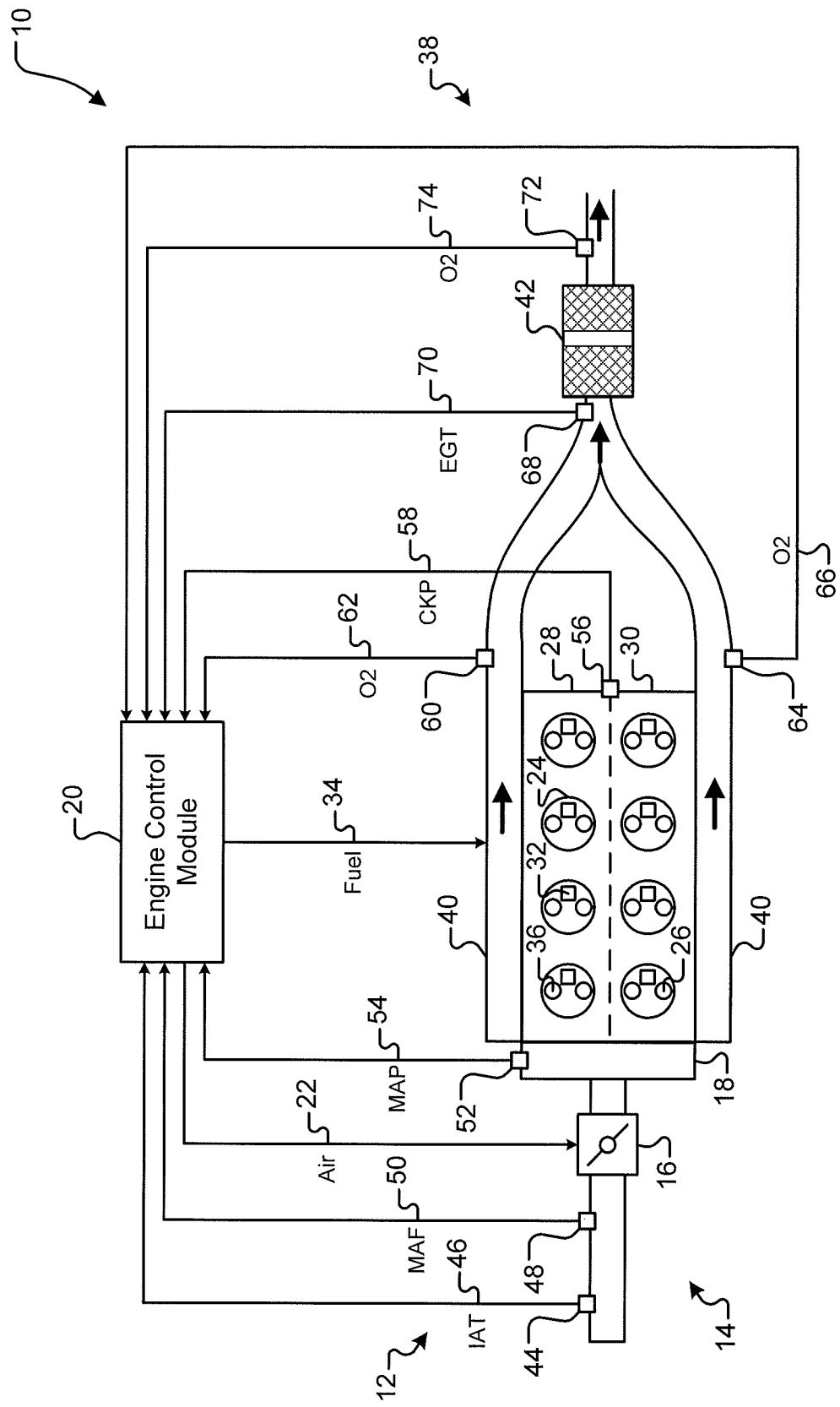
FIG. 1 is a functional block diagram of an example engine system according to the principles of the present disclosure.

An oxygen sensor may be a narrowband sensor or a wideband sensor. A narrowband sensor outputs a voltage indicating whether an air/fuel ratio is rich or lean. For example, an output voltage greater than a first voltage (e.g., 450 millivolts (mV)) may indicate a rich air/fuel ratio, and an output voltage less than the first voltage may indicate a lean air/fuel ratio. A wideband sensor outputs a voltage indicating the value of the air/fuel ratio.

An engine control module (ECM) may regulate fuel injection in an engine using closed-loop control to reduce error between a desired air/fuel ratio and an actual air/fuel ratio of the engine. The ECM may determine the desired air/fuel ratio based on engine operating conditions. The ECM may determine the actual air/fuel ratio based on the output voltage of an oxygen sensor disposed in an exhaust system of the engine.

The ECM may include a bias circuit that causes the output voltage of the oxygen sensor to indicate a rich or lean air/fuel ratio in the event of an open circuit in the oxygen sensor and/or wiring associated with the oxygen sensor. For example, an oxygen sensor signal may normally indicate a voltage between 50 mV and 850 mV, and the oxygen sensor signal may indicate a voltage as high as 1900 mV when biased. Systems and methods may diagnose a fault when the oxygen sensor signal is unexpectedly outside of the normal voltage range. However, the oxygen sensor signal may be stuck in a rich or lean state within the normal voltage range due to a fault in the oxygen sensor, a fault in wiring associated with the oxygen sensor, and/or the bias circuit. A sensor that is stuck in a rich or lean state may cause rough engine operation and/or an engine stall.

A system and method according to the principles of the present disclosure increases an error count when an actual air/fuel ratio is different from a desired air/fuel ratio, and selectively diagnoses a fault in an oxygen sensor based on the error count. The error count may be increased when the desired air/fuel ratio is lean and the actual air/fuel ratio is rich. The error count may also be increased when the desired air/fuel ratio is rich and the actual air/fuel ratio is lean. A fault in the oxygen sensor may be diagnosed when the error count is greater than a first predetermined count.

A system and method according to the principles of the present disclosure may apply a multiplier to the error count when an actual engine speed is less than a desired engine speed. The multiplier may be applied to the error count when a ratio of the actual engine speed to the desired engine speed is less than a first predetermined value and the error count is greater than a second predetermined count. The second predetermined count may be less than the first predetermined count. The second predetermined count may be predetermined to ensure that the multiplier is only applied when the actual engine speed is less than the desired engine speed due to a fuel shortage caused by a stuck rich fault or a fuel excess caused by a stuck lean fault.

A system and method according to the principles of the present disclosure may operate in an open-loop state or a pseudo-open-loop state when a faulty oxygen sensor is diagnosed. In the open-loop state, fuel injection may be controlled independent from any oxygen sensor input. In the pseudo-open-loop state, fuel injection may be controlled based on input from an oxygen sensor that is not faulty. For example, when a faulty oxygen sensor is disposed downstream from one cylinder bank of an engine, fuel injection in the cylinder bank may be controlled based on input from an oxygen sensor disposed downstream from another cylinder bank of the engine.

Diagnosing a fault in an oxygen sensor based on the error count provides diagnostic information that may be retrieved and utilized when a vehicle is serviced. Adjusting the error count using the multiplier when the actual engine speed is less than the desired engine speed accelerates diagnosis of a faulty engine sensor. Controlling fuel injection in the open-loop state or the pseudo-open-loop state when a faulty oxygen sensor is diagnosed prevents rough engine operation and an engine stall. Preventing rough engine operation and an engine stall improves customer satisfaction.

Referring now to FIG. 1, an engine system 10 includes an engine 12 that combusts an air/fuel mixture to produce drive torque for a vehicle and/or to produce torque to drive a generator to charge a battery (not shown) such as an electric vehicle battery. Air is drawn into the engine 12 through an intake system 14. The intake system 14 includes a throttle valve 16 and an intake manifold 18. The throttle valve 16 may include a butterfly valve having a rotatable blade. The throttle valve 16 opens to draw air into the intake manifold 18. An engine control module (ECM) 20 outputs a throttle control signal 22 to control the amount of air drawn into the intake manifold 18.

Air from the intake manifold 18 is drawn into cylinders 24 of the engine 12 through an intake valve 26. Although the engine 12 is depicting as having eight cylinders, the engine 12 may have additional or fewer cylinders. The engine 12 is shown as a dual bank engine, and the cylinders 24 are distributed between a first bank 28 and a second bank 30. Alternatively, the engine 12 may be a single bank engine.

One or more fuel injectors 32 inject fuel into the engine 12. Fuel may be injected into the intake manifold 18 at a central location or at multiple locations, such as near the intake valve 26 of each of the cylinders 24. In various implementations, fuel may be injected directly into the cylinders 24 or into mixing chambers associated with the cylinders 24. The ECM 20 outputs a fuel control signal 34 to control the amount of fuel injected by the fuel injectors 32.

The injected fuel mixes with air and creates an air/fuel mixture in the cylinders 24. Pistons (not shown) within the cylinders 24 compress the air/fuel mixture. The engine 12 may be a compression-ignition engine, in which case compression in the cylinders 24 ignites the air/fuel mixture. Alternatively, the engine 12 may be a spark-ignition engine, in which case spark plugs (not shown) in the cylinder 24 generate a spark that ignites the air/fuel mixture. The ECM 20 may output a spark control signal (not shown) to control spark timing (i.e., when the spark plugs generate a spark).

The byproducts of combustion are expelled through an exhaust valve 36 and exhausted from the vehicle through an exhaust system 38. The exhaust system 38 includes an exhaust manifold 40 and a three-way catalyst (TWC) 42. The TWC 42 reduces nitrogen oxide and oxidizes carbon monoxide and hydrocarbon. The TWC 42 may store oxygen when an air/fuel ratio of the engine 12 is lean, and oxygen stored in the TWC 42 may be consumed as carbon monoxide and hydrocarbon are oxidized when the air/fuel ratio is rich. The ECM 20 may oscillate the air/fuel ratio between rich and lean within a narrow band near a stoichiometric air/fuel ratio to minimize emissions.

An intake air temperature (IAT) sensor 44 measures the temperature of air drawn through the intake system 14 and generates an IAT signal 46 indicating the intake air temperature. A mass airflow (MAF) sensor 48 measures the mass flow rate of air drawn through the intake system and generates a MAF signal 50 indicating the mass flow rate of intake air. A manifold absolute pressure (MAP) sensor 52 measures pressure in the intake manifold 18 and generates a MAP signal 54 indicating the manifold pressure. A crankshaft position (CKP) sensor 56 measures the position of a crankshaft (not shown) in the engine 12 and generates a CKP signal 58 indicating the crankshaft position. The ECM 20 determines an actual speed of the engine 12 based on the CKP signal 58.

A first oxygen (O2) sensor 60 measures a first oxygen level in exhaust gas from the first bank 28 and generates a first O2 signal 62 indicating the first oxygen level. A second O2 sensor 64 measures a second oxygen level in exhaust gas from the second bank 30 and generates a second O2 signal 66 indicating the second oxygen level. An exhaust gas temperature (EGT) sensor 68 measures the temperature of exhaust gas and generates an EGT signal 70 indicating the exhaust gas temperature. A third O2 sensor 72 measures a third oxygen level in exhaust gas downstream from the TWC 42 and generates a third O2 signal 74 indicating the third oxygen level. The oxygen sensors 60, 64, 72 may be narrowband sensors or wideband sensors.

The ECM 20 receives the signals generated by the sensors discussed above and controls the engine 12 based on the signals received. The ECM 20 may diagnose a fault in the first O2 sensor 60 and/or the second O2 sensor 64. Although the ECM 20 may diagnose a fault in either of the oxygen sensors 60, 64, for simplicity, the discussion below describes the ECM 20 diagnosing a fault in the first O2 sensor 60. The ECM 20 may diagnose a fault in the second O2 sensor 64 in a similar manner.

The ECM 20 adjusts the fuel control signal 34 to achieve a desired air/fuel ratio. The ECM 20 determines an actual air/fuel ratio based on the first O2 signal 62. The ECM 20 increases an error count when the actual air/fuel ratio is different from the desired air/fuel ratio. The ECM 20 diagnoses a fault in the first O2 sensor 60 when the error count is greater than a first predetermined count.

The ECM 20 may increase the error count when the desired air/fuel ratio is lean and the actual air/fuel ratio is rich. The ECM 20 may increase the error count when the desired air/fuel ratio is rich and the actual air/fuel ratio is lean. The ECM 20 may increase the error count at a rate that is based on the actual engine speed and/or the mass flow rate of intake air indicated by the MAF signal 50.

The ECM 20 may adjust the error count when a ratio of the actual engine speed to a desired engine speed is less than a first predetermined value and the error count is greater than a second predetermined count. The second predetermined count may be less than the first predetermined count. The ECM 20 may stop adjusting the error count using the multiplier when the ratio of the actual engine speed to the desired engine speed is greater than a second predetermined value. The second predetermined value may be greater than the first predetermined value.

Figure 2:
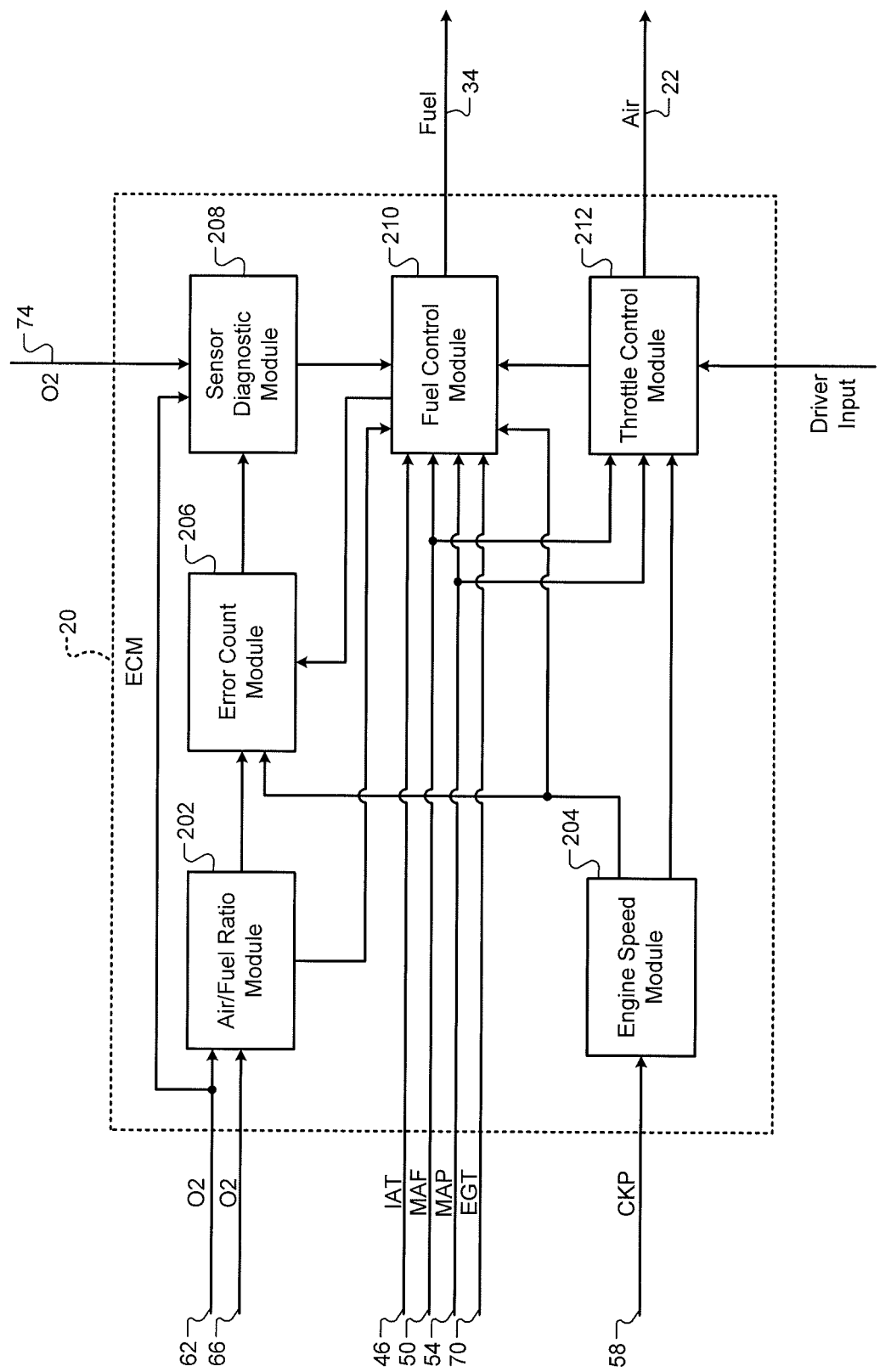
FIG. 2 is a functional block diagram of an example control system according to the principles of the present disclosure.

Referring now to FIG. 2, an example implementation of the ECM 20 includes an air/fuel ratio module 202, an engine speed module 204, an error count module 206, a sensor diagnostic module 208, a fuel control module 210, and a throttle control module 212. The air/fuel ratio module 202 determines whether an actual air/fuel ratio is rich or lean based on the first O2 signal 62. For example, the actual air/fuel ratio may be rich when the first O2 signal 62 is greater than a predetermined voltage (e.g., 450 mV) and the actual air/fuel ratio may be lean when the first O2 signal 62 is less than the predetermined voltage. The predetermined voltage may correspond to a stoichiometric air/fuel ratio. The air/fuel ratio module 202 outputs a signal indicating whether the actual air/fuel ratio is rich or lean.

The air/fuel ratio module 202 may determine the value of the actual air/fuel ratio based on the first O2 signal 62 and/or the type of fuel combusted by the engine 12. For example, the air/fuel ratio module 202 may determine that the actual air/fuel ratio is 14.7 when the first O2 signal 62 is equal to the predetermined voltage and the fuel type is gasoline. The fuel type may be predetermined, determined based on input received from a sensor (e.g., an ethanol sensor), and/or provided to the air/fuel ratio module 202 using, for example, an instrument panel and/or a service tool. The air/fuel ratio module 202 may output the value of the actual air/fuel ratio.

The engine speed module 204 determines the actual speed of the engine 12 based on the CKP signal 58. For example, the engine speed module 204 may calculate the actual engine speed based on a period that elapses as the crankshaft in the engine 12 completes one or more revolutions. The engine speed module 204 outputs the actual engine speed.

The error count module 206 increases an error count when the actual air/fuel ratio is different from a desired air/fuel ratio. The desired air/fuel ratio may be a predetermined ratio such as a stoichiometric, rich, or lean air/fuel ratio. Additionally or alternatively, the fuel control module 210 may determine the desired air/fuel ratio, as discussed below, and output the desired air/fuel ratio to the error count module 206. The error count may be a rich error count or a lean error count.

The error count module 206 may increase a rich error count when the desired air/fuel ratio is lean and the actual air/fuel ratio is rich. The error count module 206 may increase a lean error count when the desired air/fuel ratio is rich and the actual air/fuel ratio is lean. The error count module 206 may set the error count to zero when the desired air/fuel ratio and the actual air/fuel ratio are either both rich or both lean. The error count module 206 outputs the error count.

The error count module 206 may increase the error count at a rate that is based on engine operating conditions such as the mass flow rate of intake air indicated by the MAF signal 50 and the actual engine speed. The rate may be directly proportional to the engine operating conditions. The relationship between the rate and the engine operating conditions may be predetermined and may be linear or nonlinear.

The error count module 206 may apply a multiplier to the error count when the error count is greater than a first predetermined count and an error value is less than a first predetermined value. The error count module 206 may determine the error value based on the actual engine speed and the desired engine speed. For example, the error count module 206 may set the error value to a ratio of the actual engine speed to the desired engine speed. Thus, the error value may decrease as the actual engine speed decreases relative to the desired engine speed.

The error count module 206 may stop adjusting the error count using the multiplier when the error value is greater than a second predetermined value. The second predetermined value may be greater than the first predetermined value. This prevents toggling between applying the multiplier and not applying the multiplier as the error value transitions between less than and greater than the first predetermined value. Rather than stop applying the multiplier to the error count, the error count module 206 may set the multiplier to one so that applying the multiplier does not affect the error count.

The error count module 206 may set the multiplier to a predetermined value or to a value within a predetermined range (e.g., a value between 0 and 8). For example, the error count module 206 may set the multiplier to 8 to ensure that a fault is immediately diagnosed in the first O2 sensor 60 when the multiplier is applied to the error count. In another example, the error count module 206 may set the multiplier to 1.1 to accelerate diagnosis of a fault in the first O2 sensor 60 without immediately diagnosing a fault in the first O2 sensor 60 when the multiplier is applied.

The error count module 206 may determine the multiplier based on the error value (e.g., the ratio of the actual engine speed to the desired engine speed). For example, the error count module 206 may set the multiplier to 1.1 when the error value is 0.8. In another example, the error count module 206 may set the multiplier to 1.5 when the error value is 0.75.

The sensor diagnostic module 208 diagnoses a fault in the first O2 sensor 60 based on the error count. The sensor diagnostic module 208 may diagnose a stuck rich fault when the rich error count is greater than a second predetermined count. The sensor diagnostic module 208 may diagnose a stuck lean fault when the lean error count is greater than the second predetermined count. The second predetermined count may be greater than the first predetermined count. The first predetermined count, the second predetermined count, the first predetermined value, and/or the second predetermined value may be adjusted based on whether a stuck rich fault or a stuck lean fault is diagnosed. The sensor diagnostic module 208 outputs a signal indicating when a sensor fault is diagnosed. The sensor diagnostic module 208 may also set a diagnostic trouble code and/or activate a service indicator that delivers a message (e.g., light, text, chime, vibration) indicating that service is required.

The sensor diagnostic module 208 may not diagnose a fault in the first O2 sensor 60 when the first O2 signal 62 and the third O2 signal 74 indicate a lean air/fuel ratio or when the first O2 signal 62 and the third O2 signal 74 indicate a rich air/fuel ratio. The sensor diagnostic module 208 may diagnose the stuck lean fault when the lean error count is greater than the second predetermined count and the third O2 signal 74 indicates a rich air/fuel ratio. The sensor diagnostic module 208 may diagnose the stuck rich fault when the rich error count is greater than the second predetermined count and the third O2 signal 74 indicates a lean air/fuel ratio.

The fuel control module 210 outputs the fuel control signal 34 to control a rate at which fuel is injected by the fuel injectors 32. The fuel control module 210 may control the fueling rate based on the mass flow rate of intake air to achieve the desired air/fuel ratio. The fuel control module 210 may determine the desired air/fuel ratio based on engine operating conditions to minimize emissions. The engine operating conditions may include the intake air temperature, intake air mass flow rate, the manifold pressure, the engine speed, and/or the exhaust gas temperature.

The fuel control module 210 may operate in a closed-loop state when the first O2 sensor 60 is operating normally. In the closed-loop state, the fuel control module 210 adjusts the fueling rate to minimize differences between the desired air/fuel ratio and the actual air/fuel ratio. The fuel control module 210 may control fuel injection in the first bank 28 based on input received from the first O2 sensor 60 and control fuel injection in the second bank 30 based on input received from the second O2 sensor 64. Alternatively, the first O2 sensor 60 may be downstream from the first bank 28 and the second bank 30, and the fuel control module 210 may control fuel injection in the first bank 28 and the second bank 30 based on input received from first O2 sensor 60.

The fuel control module 210 may operate in an open-loop state or a pseudo-open-loop state when a fault is diagnosed in the first O2 sensor 60. The fuel control module 210 may operate in the pseudo-open-loop state when more than one O2 sensor is disposed downstream from the engine 12 and one of the O2 sensors is not faulty. The fuel control module 210 may operate in the open-loop state when only a faulty O2 sensor is disposed downstream from the engine 12.

In the open-loop state, the fuel control module 210 may control fuel injection independent from input received from the first O2 sensor 60 and the second O2 sensor 64. For example, the fuel control module 210 may control fuel injection based on a fuel map. The fuel map may specify fuel injection parameters (e.g., fuel mass, fueling rate) based on engine operating conditions. The engine operating conditions may include the intake air temperature, intake air mass flow rate, the manifold pressure, the engine speed, and/or the exhaust gas temperature.

In the pseudo-open-loop state, when a fault is diagnosed in the first O2 sensor 60, the fuel control module 210 may control fuel injection in the first bank 28 and the second bank 30 based on input received from the second O2 sensor 64. For example, the fuel control module 210 may control fuel injection in the first bank 28 and the second bank 30 to minimize differences between an actual air/fuel ratio and the desired air/fuel ratio. The air/fuel ratio module 202 may determine the actual air/fuel ratio based on the second O2 signal 66. Conversely, when a fault is diagnosed in the second O2 sensor 64, the fuel control module 210 may control fuel injection in the first bank 28 and the second bank 30 based on input received from the first O2 sensor 60.

The throttle control module 212 outputs the throttle control signal 22 to control a throttle area of the throttle valve 16. The throttle control module 212 may adjust the throttle area to minimize differences between a desired mass flow rate and an actual mass flow rate. The throttle control module 212 may determine the desired mass flow rate based on driver input. For example, the driver input may be generated based on an accelerator pedal position and/or a cruise control setting.

The throttle control module 212 may determine the actual air mass based on engine operating conditions. The engine operating conditions may include the intake air temperature, mass airflow rate, and/or the manifold pressure. The engine operating conditions may also include a throttle position. The throttle position may be measured and/or determined based on the throttle control signal 22. The throttle control module 212 may adjust the throttle position to minimize differences between a desired throttle position and an actual throttle position. The throttle control module 212 may determine the desired throttle position based on the driver input and output the resulting air mass.

Figure 3:
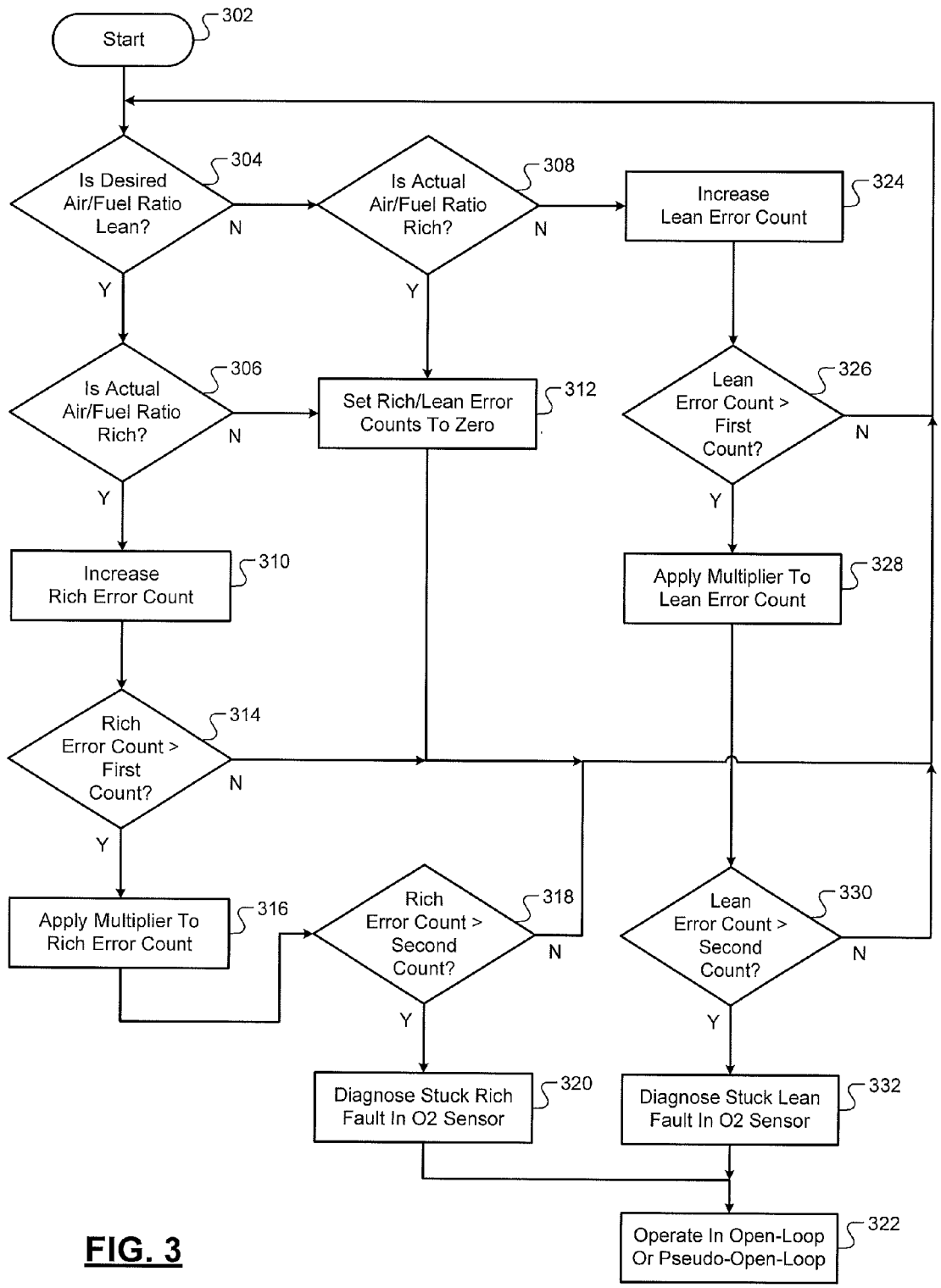
FIGS. 3 and 4 are flowcharts illustrating an example control method according to the principles of the present disclosure.

Referring now to FIG. 3, a method for diagnosing a fault in an oxygen sensor begins at 302. The oxygen sensor may be a narrowband sensor or a wideband sensor. At 304, the method determines whether a desired air/fuel ratio is lean. If 304 is true, the method continues at 306. Otherwise, the method continues at 308.

The desired air/fuel ratio may be a predetermined ratio such a stoichiometric ratio or a ratio that oscillates between rich and lean within a predetermined range. The method may determine the desired air/fuel ratio based on engine operating conditions. The engine operating conditions may include intake air temperature, intake air mass flow rate, manifold pressure, engine speed, and/or exhaust gas temperature.

At 306, the method determines whether an actual air/fuel ratio is rich. If 306 is true, the method continues at 310. Otherwise, the method continues at 312. The method determines whether the actual air/fuel ratio is rich or lean based on the output voltage of the oxygen sensor. For example, the actual air/fuel ratio may be rich when the output voltage is greater than 450 mV, and the actual air/fuel ratio may be lean when the output voltage is less than 450 mV.

At 310, the method increases a rich error count. At 314, the method determines whether the rich error count is greater than a first predetermined count. If 314 is true, the method continues at 316. Otherwise, the method continues at 304. At 316, the method applies a multiplier to the rich error count. The method may adjust the multiplier based on a desired engine speed of and an actual engine speed, as discussed in more detail below with reference to FIG. 4. For example, the method may set the multiplier to one when a ratio of the actual engine speed to the desired engine speed is greater than a predetermined ratio and set the multiplier to a value that is greater than one when the ratio is less than the predetermined ratio. Additionally or alternatively, the method may only apply the multiplier when the ratio of the actual engine speed to the desired engine speed is less than the predetermined ratio.

At 318, the method determines whether a rich error count is greater than a second predetermined count. The second predetermined count may be greater than the first predetermined count. The first predetermined count and/or the second predetermined count may be adjusted based on whether a stuck rich fault or a stuck lean fault is diagnosed. If 318 is true, the method continues at 320. Otherwise, the method continues at 304.

At 320, the method diagnoses a stuck rich fault in the oxygen sensor. The method may set a diagnostic trouble code and/or activate a service indicator when a stuck rich fault is diagnosed. The service indicator indicates that service is required using a visual message (e.g., text), an audible message (e.g., chime), and/or a tactile message (e.g., vibration).

At 322, the method operates in an open-loop state or a pseudo-open-loop state. In the open-loop state, the method controls fuel injection independent from input received from an oxygen sensor. In the pseudo-open-loop state, the method controls fuel injection based on input received from an oxygen sensor that is not faulty.

At 308, the method determines whether the actual air/fuel ratio is rich. If 308 is true, the method continues at 312. Otherwise, the method continues at 324. At 312, the method sets the rich error count and/or the lean error count to zero. At 324, the method increases a lean error count.

At 326, the method determines whether the lean error count is greater than the first predetermined count. If 326 is true, the method continues at 328. Otherwise, the method continues at 304. At 328, the method applies the multiplier to the lean error count.

At 330, the method determines whether the lean error count is greater than the second predetermined count. If 330 is true, the method continues at 332. Otherwise, the method continues at 304.

At 332, the method diagnoses a stuck lean fault in the oxygen sensor. The method may set a diagnostic trouble code and/or activate the service indicator when a stuck lean fault is diagnosed.

Figure 4:
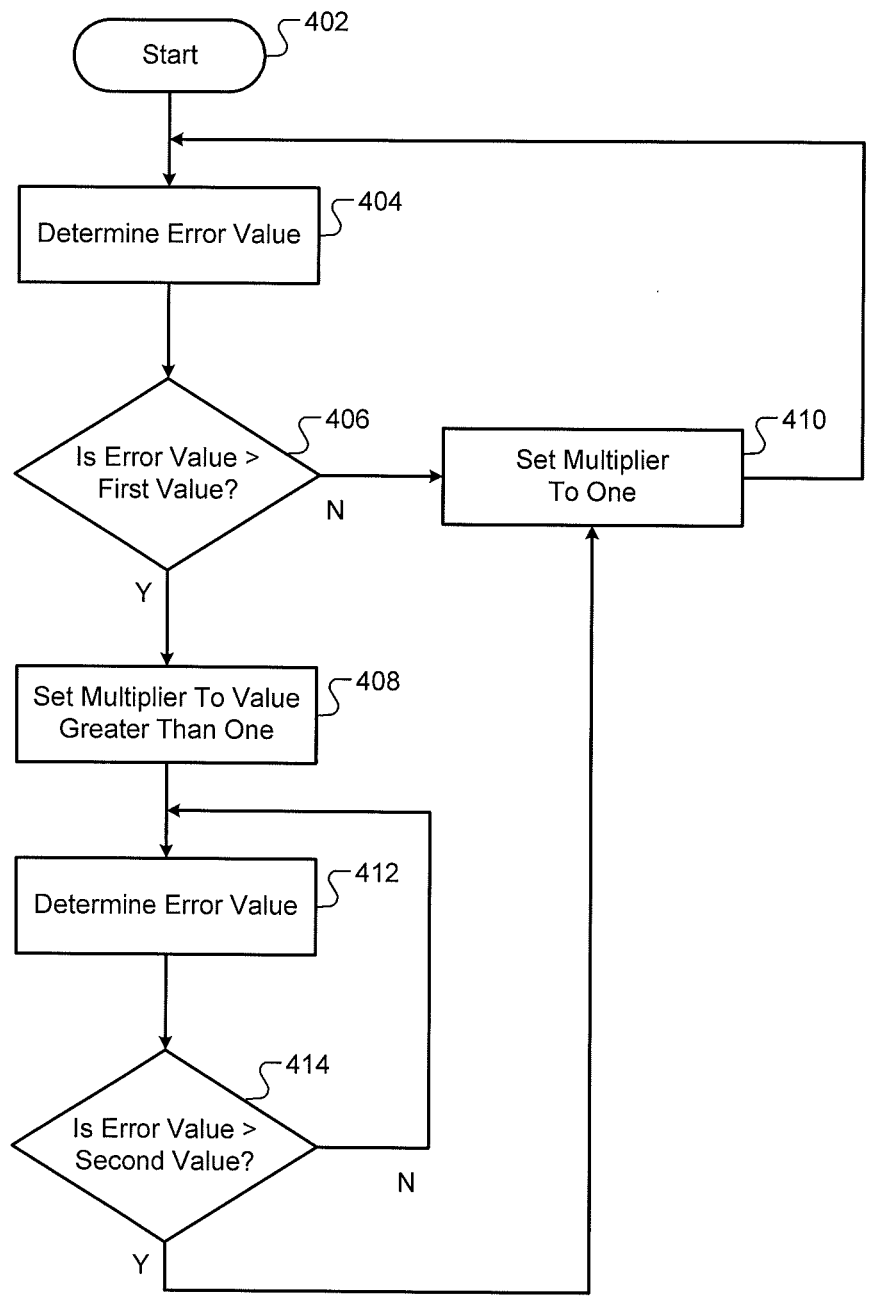

Referring now to FIG. 4, a method for determining a multiplier begins at 402. The multiplier may be used in a method for diagnosing a fault in an oxygen sensor such as the method described above with reference to FIG. 3. At 404, the method determines an error value based on an actual engine speed and a desired engine speed. The method may set the error value to a ratio of the actual engine speed to the desired engine speed.

At 406, the method determines whether the error value is greater than a first predetermined value. If 406 is true, the method continues at 408. Otherwise, the method continues at 410.

At 408, the method sets the multiplier to a value that is greater than one. The method may set the multiplier to a predetermined value or to a value within a predetermined range (e.g., a value between 0 and 8). The method may determine the multiplier based on the error value.

At 412, the method again determines the error value. At 414, the method determines whether the error value is greater than a second predetermined value. The second predetermined value may be greater than the first predetermined value. The first predetermined value and/or the second predetermined value may be adjusted based on whether a stuck rich fault or a stuck lean fault is diagnosed. If 414 is true, the method continues at 410. Otherwise, the method continues at 412. At 410, the method sets the multiplier to one.

Figure 5:
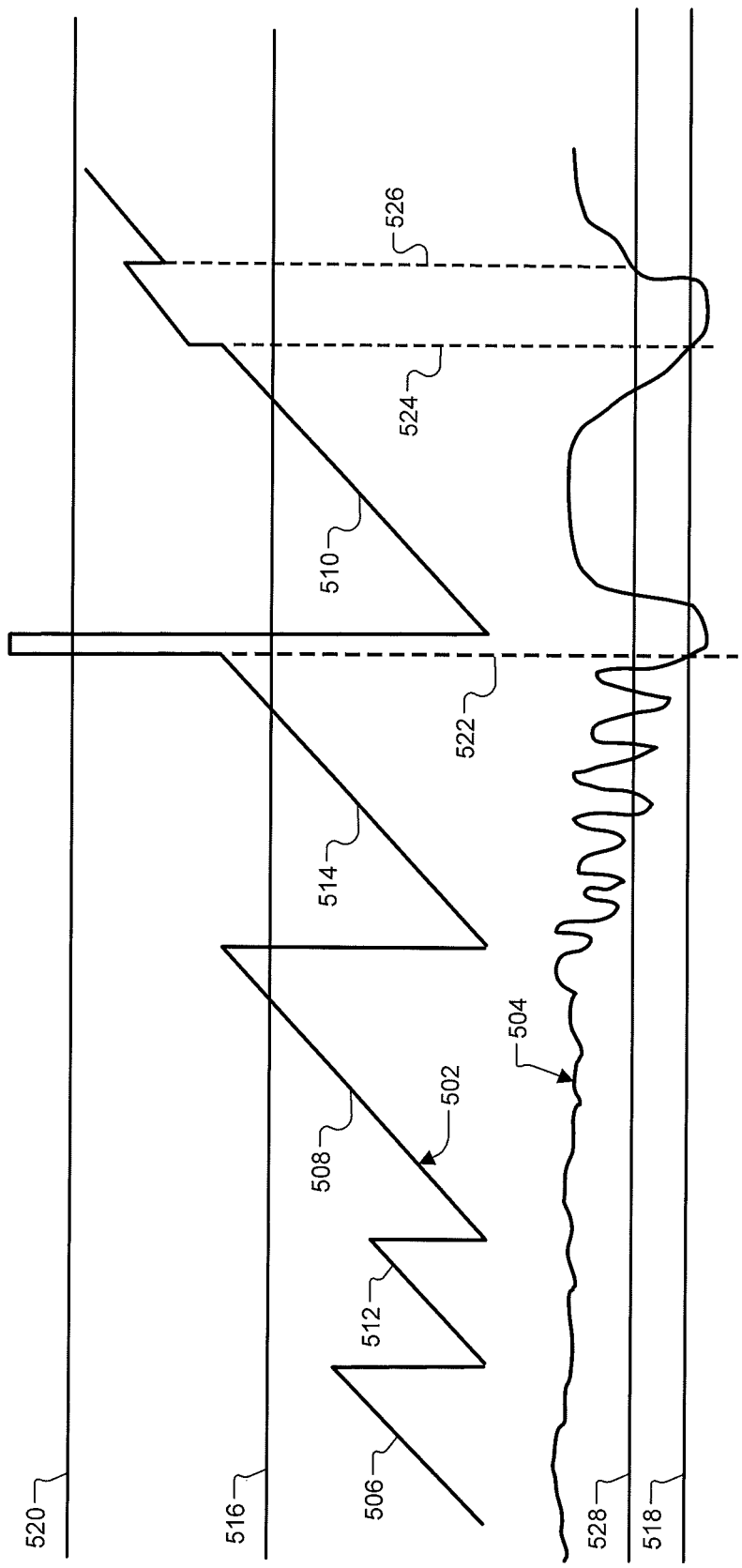
FIG. 5 is a graph illustrating example error signals according to the principles of the present disclosure.

Referring now to FIG. 5, an O2 sensor error signal 502 and an engine speed error signal 504 are illustrated. The O2 sensor error signal 502 indicates an error count that increases when an actual air/fuel ratio of an engine is different from a desired air/fuel ratio of the engine. The actual air/fuel ratio is measured using an O2 sensor that is located in an exhaust system of the engine.

The O2 sensor error signal 502 increases at 506, 508, and 510 when the desired air/fuel ratio is rich and the actual air/fuel ratio is lean. The O2 sensor error signal 502 increases at 512 and 514 when the desired air/fuel ratio is lean and the actual air/fuel ratio is rich. The engine speed error signal 504 indicates an error value that is equal to a ratio of an actual engine speed to a desired engine speed.

A multiplier is applied to the O2 sensor error signal 502 when the O2 sensor error signal 502 is greater than a first predetermined count 516 (e.g., 24) and the engine speed error signal 504 is less than a first predetermined value 518 (e.g., 0.75). An O2 sensor fault is diagnosed when the O2 sensor error signal 502 is greater than a second predetermined count 520. At 522, a first multiplier (e.g., 8) is applied to the O2 sensor error signal 502 to increase the O2 sensor error signal 502 to greater than the second predetermined count 520 (e.g., 40), causing immediate diagnosis of an O2 sensor fault.

At 524, a second multiplier (e.g., 1.1) is applied to the O2 sensor error signal 502 to accelerate diagnosis of an O2 sensor fault without causing immediate diagnosis of an O2 sensor fault. At 526, the engine speed error signal 504 increases to greater than a second predetermined value 528 (e.g., 0.85). As a result, the second multiplier is no longer applied to the O2 sensor error signal 502.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. For purposes of clarity, the same reference numbers will be used in the drawings to identify similar elements. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

As used herein, the term module may refer to, be part of, or include an Application Specific Integrated Circuit (ASIC); a discrete circuit; an integrated circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be partially or fully implemented by one or more computer programs executed by one or more processors. The computer programs include processor-executable instructions that are stored on at least one non-transitory tangible computer readable medium. The computer programs may also include and/or rely on stored data. Non-limiting examples of the non-transitory tangible computer readable medium include nonvolatile memory, volatile memory, magnetic storage, and optical storage.

What is claimed is:

1. A system comprising:
an error count module that increases an error count when an actual air/fuel ratio is different from a desired air/fuel ratio and that selectively adjusts the error count based on an actual engine speed, wherein an oxygen sensor generates a signal indicating the actual air/fuel ratio; and
a sensor diagnostic module that diagnoses a fault in the oxygen sensor when the error count is greater than a first predetermined count.

2. The system of claim 1 wherein the error count module selectively adjusts the error count using a multiplier when a ratio of the actual engine speed to a desired engine speed is less than a first predetermined value.

3. The system of claim 2 wherein the error count module determines the multiplier based on the ratio of the actual engine speed to the desired engine speed.

4. The system of claim 2 wherein the error count module adjusts the error count using the multiplier when the error count is greater than a second predetermined count, wherein the second predetermined count is less than the first predetermined count.

5. The system of claim 4 wherein the error count module stops adjusting the error count using the multiplier when the ratio is greater than a second predetermined value, wherein the second predetermined value is greater than the first predetermined value.

6. The system of claim 1 wherein the error count module increases the error count at a rate that is based on a mass flow rate of intake air and the actual engine speed.

7. The system of claim 1 wherein the error count module increases the error count when the actual air/fuel ratio is rich and the desired air/fuel ratio is lean.

8. The system of claim 1, wherein the error count module increases the error count when the actual air/fuel ratio is lean and the desired air/fuel ratio is rich.

9. The system of claim 1 wherein the error count module sets the error count to zero when the actual air/fuel ratio and the desired air/fuel ratio are one of rich and lean.

10. A system comprising:
an error count module that increases an error count at a rate that is based on at least one of a mass flow rate of intake air and engine speed when an actual air/fuel ratio is different from a desired air/fuel ratio, wherein an oxygen sensor generates a signal indicating the actual air/fuel ratio; and
a sensor diagnostic module that diagnoses a fault in the oxygen sensor when the error count is greater than a predetermined count.

11. A method comprising:
increasing an error count when an actual air/fuel ratio is different from a desired air/fuel ratio, wherein an oxygen sensor generates a signal indicating the actual air/fuel ratio;
selectively adjusting the error count based on an actual engine speed; and
diagnosing a fault in the oxygen sensor when the error count is greater than a first predetermined count.

12. The method of claim 11 further comprising selectively adjusting the error count using a multiplier when a ratio of the actual engine speed to a desired engine speed is less than a first predetermined value.

13. The method of claim 12 further comprising determining the multiplier based on the ratio of the actual engine speed to the desired engine speed.

14. The method of claim 12 further comprising adjusting the error count using the multiplier when the error count is greater than a second predetermined count, wherein the second predetermined count is less than the first predetermined count.

15. The method of claim 14 further comprising stopping adjustment of the error count using the multiplier when the ratio is greater than a second predetermined value, wherein the second predetermined value is greater than the first predetermined value.

16. The method of claim 11 further comprising increasing the error count at a rate that is based on a mass flow rate of intake air and the actual engine speed.

17. The method of claim 11 further comprising increasing the error count when the actual air/fuel ratio is rich and the desired air/fuel ratio is lean.

18. The method of claim 11, further comprising increasing the error count when the actual air/fuel ratio is lean and the desired air/fuel ratio is rich.

19. The method of claim 11 further comprising setting the error count to zero when the actual air/fuel ratio and the desired air/fuel ratio are one of rich and lean.

20. A method comprising:
increasing an error count at a rate that is based on at least one of a mass flow rate of intake air and engine speed when an actual air/fuel ratio is different from a desired air/fuel ratio, wherein an oxygen sensor generates a signal indicating the actual air/fuel ratio; and
diagnosing a fault in the oxygen sensor when the error count is greater than a predetermined count.

* * * * *